United States Patent [19]

Ito et al.

[11] 4,447,240

[45] May 8, 1984

[54] DISPOSABLE DIAPER

[75] Inventors: Osamu Ito, Utsunomiya; Kazunori Nishizawa, Funabashi, both of Japan

[73] Assignee: Kao Soap Co., Ltd., Tokyo, Japan

[21] Appl. No.: 302,271

[22] Filed: Sep. 15, 1981

[30] Foreign Application Priority Data

Sep. 22, 1980 [JP] Japan ............................. 55-132064

[51] Int. Cl.³ .............................................. A41B 13/02
[52] U.S. Cl. .................................... 604/385; 604/375
[58] Field of Search ...................... 128/284, 286, 287; 604/368, 372, 373, 374, 375, 376, 377, 384, 385

[56] References Cited

U.S. PATENT DOCUMENTS 2,691,391 10/1954 Jamison et al. ...................... 128/284
4,055,184 10/1977 Karami ................................ 128/287
4,253,461 3/1981 Strickland et al. ................. 128/287

Primary Examiner—C. Fred Rosenbaum
Assistant Examiner—Sherri E. Vinyard
Attorney, Agent, or Firm—Flynn, Thiel, Boutell & Tanis

[57] ABSTRACT

A disposable diaper is disclosed which comprises a liquid-permeable surface sheet, a liquid-impermeable back face sheet and a water-absorbing layer disposed between said sheets, wherein water-absorbing shrinkable fibers, the length of which is reduced on contact with water to impart elasticity to the fibers, are fixed across the central portion of the diaper in the lengthwise direction of the diaper without being lapped over the water-absorbing layer and said water-absorbing layer is connected to said water-absorbing shrinkable fibers by cellulose fibers.

10 Claims, 6 Drawing Figures

DISPOSABLE DIAPER

The present invention relates to a disposable diaper in which the side edge portion falling in contact with the crotch portion is shrunk and shows elasticity after absorption of a liquid. More specifically, the present invention relates to such a disposable diaper in which the efficiency of manifestation of elasticity by contraction on absorption of water is especially considered.

Various disposable diapers have heretofore been proposed. In most of the conventional disposable diapers, a sheet obtained by kneading 3 to 5% of titanium oxide into low density polyethylene, forming the composition into a film having a thickness of about $25\mu$ according to a known method and embossing the resulting film is used as the liquid-impermeable back face sheet. A structure of fluff pulp stably surrounded by a tissue is used as the water-absorbing layer and placed on the liquid-impermeable back face sheet. A structure in which a solid is fixed, which solid is capable of absorbing water in an amount at least several times the weight of the solid per se, for example, a super water-absorbing polymer such as a polyacrylic acid derivative or carboxymethylated pulp fiber, has recently been proposed.

A nonwoven fabric is ordinarily used as a liquid-permeable porous sheet (surface sheet) to be lapped over the water-absorbing layer. Nonwoven fabrics mainly used in Japan are made of polyester fibers having a base weight of 15 to 20 $g/m^2$. A polyethylene film having fine holes formed therein is marketed as the surface sheet.

A disposable diaper is ordinarily formed using an adhesive tape to fix the foregoing elements to the body. Recently, a disposable diaper comprising a zigzag portion formed along the side edge in the lengthwise direction using an elastomer to fix the diaper closely to the crotch of a wearer has been proposed as disclosed in Japanese Patent Publication No. 40267/77 and Japanese Patent Application Laid-Open Specifications Nos. 115939/79 and 120045/77. In the disposable diaper of this type, since the elastic shrinkage force of an elastomer such as rubber is used, when the diaper is worn for a long time, the wearing portion is closed and becomes stuffy by the contracting action of rubber. Furthermore, the diaper has a tight feel to a wearer. However, such diaper formed by using an elastomer fits well to a wearer and is advantageous in that the body fluid hardly leaks out. Accordingly, diapers of this type are now marketed in large quantities.

We previously proposed a water-absorbing shrinkable fiber which shrinks and shows elasticity for the first time when it absorbs water (Japanese Patent Application No. 83390/80 corresponding to U.S. Ser. No. 274,124, filed June 16, 1981). We found that when this water-absorbing shrinkable fiber is arranged along the lengthwise direction of the side edge portion instead of the above-mentioned elastomer, the diaper shrinks only when it absorbs water and the diaper gets fit to the body of the wearer in a good condition, and we proposed such disposable diaper (Japanese Patent Application No. 108583/80 corresponding to U.S. Pat. No. 4,357,938). When this disposable diaper is worn, the crotch portion is not closed while the quantity of the absorbed liquid is small, and a stuffy or pressing feel is moderated. However, in a disposable diaper having the above-mentioned structure, when a liquid guided from the water-absorbing layer is not smoothly transferred to the water-absorbing shrinkable fiber, for example, when a large quantity of a liquid passes through the side edge portion at one time, manifestation of the water-absorbing and shrinking actions is delayed and there occurs a risk of leakage of the liquid. In fact, it is often observed that such undesirable phenomenon takes place when such diaper is actually used.

We made studies with a view to eliminating these defects and succeeded in developing a disposable diaper in which the side edge portions are shrunk and contracted with good timing and a large quantity of the body fluid can be absorbed and retained in the water-absorbing layer. Thus, we have now completed the present invention.

More specifically, in accordance with the present invention, there is provided a disposable diaper comprising a liquid-permeable surface sheet, a liquid-impermeable back face sheet and a water-absorbing layer disposed between both the sheets, wherein a pair of bundles of water-absorbing shrinkable fibers, the lengths of which bundles are contracted on contact with water to impart elasticity to the fibers, are fixed across the central portion in the lengthwise direction of the disposable diaper without being lapped over the water-absorbing layer and said water-absorbing layer is connected to said bundles of water-absorbing shrinkable fibers through cellulose fibers.

In the present invention, as the structure in which the water-absorbing layer is connected to the bundles of water-absorbing shrinkable fibers through cellulose fibers, there can be mentioned, for example, a structure in which the water-absorbing layer containing cellulose fibers is contiguous to bundles of water-absorbing shrinkable fibers, and a structure in which the water-absorbing layer and the bundles of water-absorbing shrinkable fibers are contiguous to cellulose fibers such as water-absorbing paper or rayon yarn.

The absorption of a liquid by a disposable diaper in use and the state of water absorption and shrinkage will now be described with reference to an embodiment where the diaper is worn by a baby.

For newborn babies to 1.5-years-old babies, it is said that the quantity of urine discharged at one time is about 30 to 60 cc, and this quantity varies according to the season. When disposable diapers now marketed are freely used according to customary procedures and the amount of urine absorbed by one diaper is measured, this amount is about 100 cc in the case of 10-months-old babies. When the age is taken into account, it is judged that this quantity corresponds to two excretions. Accordingly, if absorption of the liquid discharged at first excretion is sufficiently performed, the water-absorbing fibers are not substantially wet and water absorption or shrinkage is not caused unless water is absorbed preferentially on the left or right side, and the water-absorbing shrinkable fibers on the preferentially water-absorbing side can be adjusted. When the second excretion is made, shrinkage immediately takes place. In the present invention, the cellulose fibers have the function of guiding water promptly and uniformly to the water-absorbing shrinkable fiber bundles of a length of about 20 cm formed along the side edges in parallel to the lengthwise direction of the disposable diaper. As such cellulose fiber, a water-absorbing paper is preferably used. Long fibers, for example, rayon yarns, may also be used in some cases.

In the present invention, as the bundles of water-absorbing shrinkable fiber, there can be used, for example, yarns of modification products of cellulose fibers of cotton, rayon and the like, such as carboxymethylated cotton, methylated cotton, ethylated cotton, hydroxyethylated cotton, sulfated cotton, sulfonated cotton, phosphated cotton, cationized cotton, amphoterically ionized cotton, cellulose fibers grafted with sodium acrylate, acrylic acid, acrylonitrile and acrylamide and crosslinked products thereof, and similar modification products of wool, silk and the like and modified synthetic fibers, such as partially saponified acrylonitrile type fibers and fibers of Vinylon partially esterified with maleic acid.

The present invention will now be described in detail with reference to the accompanying drawings.

Figure 1:
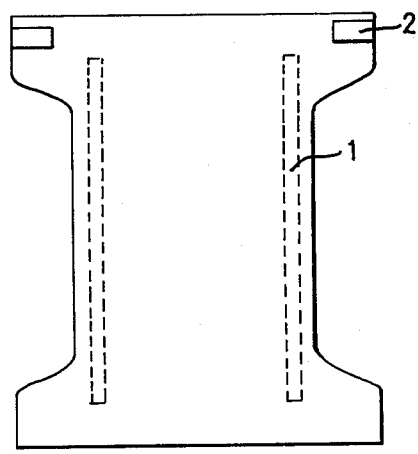
FIG. 1 is a top plan view showing one embodiment of the disposable diaper of the present invention.
Figure 2:
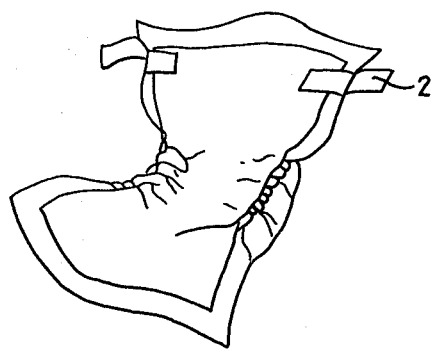
FIG. 2 is a perspective view illustrating the state where the bundles of water-absorbing shrinkable fiber absorb water.

FIG. 1 is a top plan view showing the disposable diaper of the present invention in which bundles of water-absorbing fibers 1 are arranged along the lengthwise direction of the side edge portions of the diaper. When this diaper absorbs water, the side edge portions shrink and the diaper becomes fit to the body of the wearer as shown in FIG. 2. Reference numeral 2 represents an adhesive tape for fixing the diaper to the body. FIGS. 3 through 6 illustrate embodiments of the disposable diaper according to the present invention.

Figure 3:
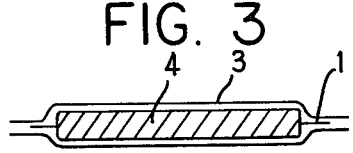
FIGS. 3 through 6 are sectional views, along portions containing cellulose fibers, illustrating embodiments of the disposable diaper of the present invention.

In the embodiment shown in FIG. 3, a water-absorbing layer 4 located between a surface sheet 3 and a back face sheet 5 is brought into contact with bundles of water-absorbing shrinkable fibers 1. Urine discharged from the wearer passes through the liquid-permeable surface sheet 3 (ordinarily a nonwoven fabric) and is absorbed and diffused in the water-absorbing layer 4 (fluff pulp, a combination of fluff pulp and a super absorbing polymer or a structure formed of a highly absorbing polymer). The liquid is guided to the bundles of water-absorbing shrinkable fibers 1 by cellulose fibers contained in the water-absorbing layer 4 and the bundles of water-absorbing shrinkable fibers 1 shrink and the diaper becomes fit to the body of the wearer. When urine is then discharged, since the side edge portion is contracted, leakage of the liquid hardly occurs.

Figure 4:
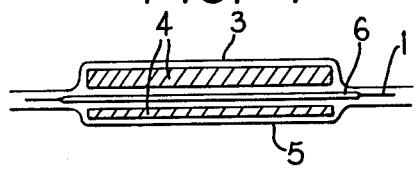
Figure 5:
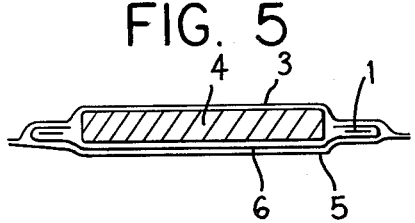
Figure 6:
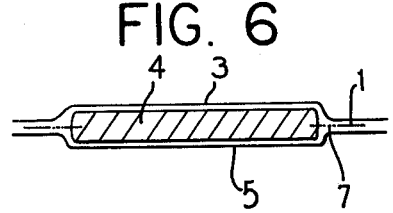

FIGS. 4 through 6 illustrate embodiments where a water-absorbing layer 4 is connected to the bundles of water-absorbing shrinkable fibers 1 through a water-absorbing paper 6 or rayon yarn 7. As in the embodiment shown in FIG. 3, urine absorbed and diffused in the water-absorbing layer 4 is promptly and uniformly guided to the bundles of water-absorbing shrinkable fibers 1 and the side edge portion is contracted. A water-absorbing paper is most preferred as the cellulose fiber, but a rayon yarn or a cellulose-type nonwoven fabric may also be used.

The present invention will now be described in detail with reference to the following Examples. The following materials were used in these Examples.

MATERIALS USED

Water-absorbing shrinkable fiber 1: bundle of 10 mix-twisted yarns formed by twisting a cotton yarn (count number=20) with a carboxymethylated cotton yarn (count number=20)

Liquid-permeable surface sheet 3: nonwoven fabric (base weight of 20 g/m$^2$) formed by fusion bonding of polyesters and ES fibers Water-absorbing layer 4: fluff pulp (36 g) wrapped with a tissue having a base weight of 20 g/m$^2$ Liquid-impermeable back face sheet 5: polyethylene film (base weight=25 g/m$^2$)

Water-absorbing paper 6: one having a base weight of 20 g/m$^2$

Rayon yarn 7: one having a count number of 10

EXAMPLE 1

The above materials 1, 3, 4 and 5 were arranged so that the bundles of water-absorbing fibers 1 were contiguous to the water-absorbing layer 4 as shown in FIG. 3, whereby a disposable diaper as shown in FIG. 1 was obtained.

EXAMPLE 2

The above materials 1, 3, 4, 5 and 6 were arranged as shown in FIG. 4 to obtain a disposable diaper as shown in FIG. 1.

EXAMPLE 3

The above materials 1, 3, 4, 5 and 6 were arranged as shown in FIG. 5 to obtain a disposable diaper as shown in FIG. 1.

EXAMPLE 4

The above materials 1, 3, 4, 5 and 7 were arranged as shown in FIG. 6 so that the rayon yarn 7 was located between the bundles of water-absorbing shrinkable fibers 1 and the water-absorbing layer 4, whereby a disposable diaper as shown in FIG. 1, in which the liquid was guided to the bundles of water-absorbing fibers 1 through the rayon yarn 7, was obtained.

COMPARATIVE EXAMPLE 1

A disposable diaper was formed in the same manner as described in Example 4 except that the rayon yarn 7 was not used.

A synthetic urine having a surface tension of 50±3 dyne/cm was absorbed in each of the diapers prepared in the foregoing Examples and Comparative Example, and the amount of the liquid absorbed and the percent shrinkage of the side edge portion were measured. The obtained results are shown in Table 1.

TABLE 1

| | Percent Shrinkage** (%) | | | |
| --- | --- | --- | --- | --- |
| | Amount (g) of Synthetic Urine | | | |
| Example No. | 60 | 100 | 140 | 180 |
| 1 | 0 | 8.0 | 15.7 | 16.0 |
| 2* | 2.5 | 22.5 | 24.9 | 25.1 |
| 3* | 1.0 | 23.5 | 25.4 | 26.0 |
| 4* | 0 | 19.8 | 24.0 | 24.5 |
| Comparative Example 1* | 0 | 0 | 0 | 26.5*** (leakage from edge) |

Note
*In Examples 2, 3 and 4 and Comparative Example 1, the distance between the water-absorbing layer 4 and the bundles of water-absorbing fibers 1 was adjusted to 30 mm

**Percent shrinkage = $\dfrac{\text{(original length} - \text{length after shrinkage)}}{\text{original length}} \times 100$

***Liquid leaked out from the edge and shrinkage was then caused.

From the foregoing results, it will readily be understood that if the bundles of water-absorbing shrinkable fibers are kept in contact with the water-absorbing layer through the cellulose fiber, elasticity by shrinkage is manifested even when the amount absorbed of the liquid is small, and leakage of the liquid is effectively prevented by the bundles of water-absorbing shrinkable fibers.

The embodiments of the invention in which an exclusive property or privilege is claimed are defined as follows:

1. A disposable diaper comprising: a liquid-permeable surface sheet; a liquid-impermeable back sheet; a water-absorbing layer located between said sheets; a pair of bundles of water-absorbing shrinkable fibers which shrink in the lengthwise direction of the fibers and are rendered elastic on absorption of water, said bundles of water-absorbing shrinkable fibers being fixed along the edges in the central portion of said diaper and extending in the lengthwise direction of said disposable diaper and located so that said bundles of water-absorbing shrinkable fibers are not placed on the water-absorbing layer but are capable of being wetted when said diaper is wetted; and cellulose fibers extending between and connecting said water-absorbing layer and said bundles of water-absorbing shrinkable fibers for smoothly transferring liquid from said water-absorbing layer to said bundles of water-absorbing shrinkable fibers, wherein said cellulose fibers comprise an absorbent paper extending from said water-absorbing layer to said bundles of water-absorbing shrinkable fibers for transferring liquid from said water-absorbing layer to said shrinkable fibers, a central portion of said absorbent paper being interposed between said water-absorbing layer and said liquid-impermeable back sheet, said paper having lateral edge portions which extend beyond the edges of said water-absorbing layer such that said lateral edge portions of said absorbent paper are interposed between said bundles of water-absorbing shrinkable fibers and said liquid-impermeable back sheet, and the lateral ends of said lateral edge portions comprise flap portions of each of said lateral edge portions, which flap portions are folded over said bundles of water-absorbing shrinkable fibers and thereby interposed between said bundles of water-absorbing shrinkable fibers and said liquid-permeable surface sheet.

2. A disposable diaper as claimed in claim 1, wherein said bundles are comprised of water-absorbing shrinkable fibers and cellulose fibers blended therewith.

3. A disposable diaper comprising: a liquid-permeable surface sheet; a liquid-impermeable back sheet; a water-absorbing layer located between said sheets; a pair of bundles of water-absorbing shrinkable fibers which shrink in the lengthwise direction of the fibers and are rendered elastic on absorption of water, said bundles of water-absorbing shrinkable fibers being fixed along the edges in the central portion of said diaper and extending in the lengthwise direction of said disposable diaper and located so that said bundles of water-absorbing shrinkable fibers are not placed on the water-absorbing layer but are capable of being wetted when said diaper is wetted; and cellulose fibers extending between and connecting said water-absorbing layer and said bundles of water-absorbing shrinkable fibers for smoothly transferring liquid from said water-absorbing layer to said bundles of water-absorbing shrinkable fibers, wherein said water-absorbing layer is comprised of two sub-layers, said cellulose fibers comprising a unitary layer of absorbent paper extending through said water-absorbing layer to said bundles of water-absorbing shrinkable fibers located on opposite lateral sides of said water-absorbing layer for transferring liquid from said water-absorbing layer to said shrinkable fibers, the central portion of said absorbent paper being disposed between said sub-layers.

4. A disposable diaper as claimed in claim 3, wherein said bundles are comprised of water-absorbing shrinkable fibers and cellulose fibers blended therewith.

5. A disposable diaper comprising: a liquid-permeable surface sheet; a liquid-impermeable back sheet; a water-absorbing layer located between said sheets; a pair of bundles of water-absorbing shrinkable fibers which shrink in the lengthwise direction of the fibers and are rendered elastic on absorption of water, said bundles of water-absorbing shrinkable fibers being fixed along the edges in the central portion of said diaper and extending in the lengthwise direction of said disposable diaper and located so that said bundles of water-absorbing shrinkable fibers are not placed on the water-absorbing layer but are capable of being wetted when said diaper is wetted; and cellulose fibers extending between and connecting said water-absorbing layer and said bundles of water-absorbing shrinkable fibers for smoothly transferring liquid from said water-absorbing layer to said bundles of water-absorbing shrinkable fibers, wherein said bundles of water-absorbing shrinkable fibers are spaced from the lateral edges of said water-absorbing layer, and said cellulose fibers consist essentially of rayon yarns which extend between and connect said water-absorbing layer and said bundles of water-absorbing shrinkable fibers.

6. A disposable diaper as claimed in claim 5, wherein said bundles are comprised of water-absorbing shrinkable fibers and cellulose fibers blended therewith.

7. A disposable diaper comprising: a liquid-permeable surface sheet; a liquid-impermeable back sheet; a water-absorbing layer located between said sheets; a pair of bundles of water-absorbing shrinkable fibers which shrink in the lengthwise direction of the fibers and are rendered elastic on absorption of water, said bundles of water-absorbing shrinkable fibers being fixed along the edges in the central portion of said diaper and extending in the lengthwise direction of said disposable diaper and located so that said bundles of water-absorbing shrinkable fibers are not placed on the water-absorbing layer but are capable of being wetted when said diaper is wetted; and cellulose fibers extending between and connecting said water-absorbing layer and said bundles of water-absorbing shrinkable fibers for smoothly transferring liquid from said water-absorbing layer to said bundles of water-absorbing shrinkable fibers, wherein the laterally inner edges of said bundles of water-absorbing shrinkable fibers are contiguous with the lateral outer edges of said water-absorbing layer.

8. A disposable diaper as claimed in claim 7, wherein said bundles are comprised of water-absorbing shrinkable fibers and cellulose fibers blended therewith.

9. In a disposable diaper comprising a liquid-absorbing layer located between a liquid-permeable surface sheet and a liquid-impermeable backing sheet, the side edges of said liquid-absorbing layer being laterally inwardly spaced from the side edges of said sheets, said diaper having a central portion adapted to be extended between the legs of a wearer and having front and rear portions adapted to be secured together around the waist of the wearer and wherein the liquid permeable surface sheet is adapted to be disposed facing the body of the wearer and the liquid-impermeable backing sheet is adapted to be disposed facing away from the body of the wearer, the improvement which comprises: a pair of strips disposed close to the respective side edges of said sheets in the central portion of said diaper and extending lengthwise therealong, said strips being located between said sheets and spaced outwardly from the lateral edges of said liquid-absorbing layer, said strips comprising mixed bundles of liquid-absorbing, lengthwise shrinkable fibers which shrink and become elastic when they are wetted with liquid and cellulose fibers which do not substantially shrink when they are wetted with said liquid, so that when said strips absorb liquid and shrink, the side edges of said central portion of said diaper are drawn into snug engagement with the wearer's legs to minimize liquid leakage; and cellulose fibers extending between and connecting said liquid-absorbing layer and said strips for smoothly transferring liquid from said liquid-absorbing layer to said strips.

10. A disposable diaper as claimed in claim 9, wherein said liquid absorbing shrinkable fibers are formed of one or more materials selected from the group consisting of carboxymethylated cotton, methylated cotton, ethylated cotton, hydroxyethylated cotton, sulfated cotton, sulfonated cotton, phosphated cotton, cationized cotton, amphoterically ionized cotton, cellulose fibers grafted with sodium acrylate, acrylic acid, acrylonitrile, acrylamide, crosslinking products of the foregoing materials, partially saponified acrylonitrile fibers, and fibers of vinyl alcohol partially esterified with maleic acid.

* * * * *